United States Patent
Delevallee et al.

[11] Patent Number: 4,880,803
[45] Date of Patent: Nov. 14, 1989

[54] METHOD OF INDUCING IMMUNOSTIMULATING ACTIVITY

[75] Inventors: Francoise Delevallee, Fontenay Sous Bois; Roger Deraedt, Pavillons Sous Bois; Josette Benzoni, Livry Gargan, all of France

[73] Assignee: Roussel Uclaf, Paris, France

[21] Appl. No.: 103,919

[22] Filed: Oct. 1, 1987

Related U.S. Application Data

[63] Continuation of Ser. No. 898,241, Aug. 8, 1986, abandoned.

[30] Foreign Application Priority Data

Aug. 22, 1985 [FR] France ................... 85 12619

[51] Int. Cl.$^4$ ............... A61K 31/535; A61K 31/50; A61K 31/495; A61K 31/40
[52] U.S. Cl. .................. 514/232.8; 514/253; 514/410
[58] Field of Search ............ 514/234, 253, 410

[56] References Cited

U.S. PATENT DOCUMENTS 3,998,823 12/1976 Taylor et al. .............. 544/142

Primary Examiner—Jerome D. Goldberg
Attorney, Agent, or Firm—Bierman & Muserlian

[57] ABSTRACT

A method of inducing immunostimulating activity in warm-blooded animals comprising administering to warm-blooded animals an immunostimulating amount of at least one maleo-pimaric acid compound of the formula

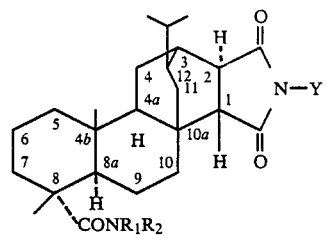

wherein $R_1$ and $R_2$ together with the nitrogen to which they are attached form an optionally substituted saturated heterocycle optionally containing at least one other heteroatom, Y is selected from the group consisting of hydrogen, amino, alkyl of 1 to 5 carbon atoms optionally substituted with at least one hydroxy, dialkylamino with alkyl of 1 to 5 carbon atoms, alkoxy carbonyl of 2 to 5 carbon atoms, acyl of an organic carboxylic acid of 1 to 5 carbon atoms and

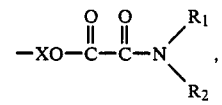

X is an alkylene of 1 to 5 carbon atoms and $R_1$ and $R_2$ have the above definition.

5 Claims, No Drawings

METHOD OF INDUCING IMMUNOSTIMULATING ACTIVITY

PRIOR APPLICATION

This application is a continuation of U.S. patent application Ser. No. 898,241, filed Aug. 18, 1986 now abandoned.

STATE OF THE ART

U.S. Pat. No. 3,998,823 describes novel maleopimaric acid compounds having a hepato-protective activity.

OBJECTS OF THE INVENTION

It is an object of the invention to provide a novel method of inducing immunostimulating activity in warm-blooded animals including humans.

This and other objects and advantages of the invention will become obvious from the following detailed description.

THE INVENTION

The novel method of the invention of inducing immunostimulating activity in warm-blodded animals comprises administering to warm-blooded animals an immunostimulating amount of at least one maleopimaric acid compound of the formula

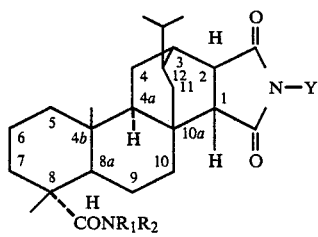

wherein $R_1$ and $R_2$ together with the nitrogen to which they are attached form an optionally substituted saturated heterocycle optionally containing at least one other heteroatom, Y is selected from the group consisting of hydrogen, amino, alkyl of 1 to 5 carbon atoms cptionally substituted with at least one hydroxy, dialkylamino with alkyl of 1 to 5 carbon atoms, alkoxy carbonyl of 2 to 5 carbon atoms, acyl of an organic carboxylic acid of 1 to 5 carbon atoms and

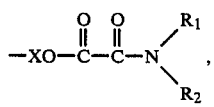

X is an alkylene of 1 to 5 carbon atoms and $R_1$ and $R_2$ have the above definition. The usual daily dose is 0,30 to 40 mg/kg depending on the specific compound, the method of administration and the condition treated. The compounds may be administered orally, rectally, parenterally or topically.

While U.S. Pat. No. 3,998,823 describes the maleopimaric acid compounds as having hepato-protecting properties, this would in no way suggest to one skilled in t:he art that the compounds of formula I would have remarkable immuno-modulating properties. Immunomodulator is understood to "regulate the immunizing reactions by inhibiting them or stimulating them" (Messieurs Garnier—Delamare—Dictionnaire des termes techniques de Medicine p. 421-21st edition 1985).

$R_1$ and $R_2$ together with the nitrogen atom may for example, be a saturated heterocycle containing from 4 to 6 carbon atoms such as, for example, morpholino, piperidino, piperazin-1-yl, pyrrolidino or hexamethylene imino, this latter group being able to carry a substitutent at either on the carbon atoms, i.e., the substituent being alkyl, hydroxyalkyl or phenyl, or on the nitrogen with the substituent then being phenyl, alkyloxycarbonyl, sulfonyl or acyl, such alkyl, alkyloxy or acyl containing at the most 5 carbon atoms. Y may be, for example, hydroxyalkyl, dialkylaminoalkyl or alkyloxycarbonyl with the alkyls containing 1 to 5 carbon atoms.

Among the preferred compounds of the invention are those of formula I wherein $R_1$ and $R_2$ together with the nitrogen atom represent pyrrolidino, morpholino, piperazin-1-yl, 4-alkyl-piperazin-1-yl or 4-hydroxyalkyl-piperazin-1-yl group and those wherein Y is hydrogen, amino or $\beta$-hydroxyethyl and preferably those of formula I wherein $R_1$ and $R_2$ together with the nitrogen atom are morpholino and those wherein Y is hydrogen or $\beta$-hydroxy-ethyl.

The preferred compounds of formula I are $8\beta$-morpholinocarbonyl-4b$\alpha$8$\alpha$-dimethyl-12-isopropyl-1$\beta$,2$\beta$,3$\beta$4,4a$\beta$-4b $\beta$,5,6,7,8,8a $\beta$, 9,10,10a-tetradecahydro-3,10a-ethenophenantro-[1,2-c]-1'-(2-hydroxyethyl)-2',5'-pyrrolidinedione and 8$\beta$-(morpholino carbonyl)-4b $\alpha$, 8$\alpha$-dimethyl-12-isopropyl-1$\beta$,2$\beta$,3$\beta$, 4,4a$\beta$, 5,6,7,8,8a$\beta$, 9,10,10a-tetradecahydro-3,10a-ethenophenantro-[1,2-c]-2',5'-pyrrolidinedione.

The derivatives with the formula I possess remarkable immuno-modulating properties and are further distinguished by a very weak toxicity and a remarkable tolérance. Because of these properties, the immuno-modulating compositions may be administered as prophylactic or curative means. They are useful in the treatment of auto-immune diseases, whether concerned with non-specific attacks on organs (rheumatoid polyarthritis, erythematous lupus, hemolytic anemia, auto-immune leukopenia, etc.) or with specific diseases of organs (thyroiditis, Graves' disease, Addison's disease, disseminated sclerosis, pemphigus, hemorrhagic rectocolitis, certain nephropathies etc.). The compositions are also useful in the treatment of hemopathies, of AIDS, of viral and microbial infections, particularly chronic and recurrent (bronchitis, influenza, etc.), diseases of the oral cavities, etc. They can be adjuvants of viral therapy and of antibiotic therapy.

The are also useful in the treatment of numerous secondary or acquired immune deficiencies observed during very different affections: deficiencies associated with metabolic disturbances, deficiencies of iatrogenic origin (corticoids, ionising radiations), deficiencies observed in those suffering from severe burns, etc.

The compositions may be in the form of tablets, dragees, gelules, capsules, granules, gels, ointments, creams and injectable solutions or suspensions. Examples of suitable excipients are talc, gum arabic, lactose, starch, magnesium stearate, cocoa butter, aqueous or non aqueous vehicles, fatty substances of animal or vegetable origin, paraffin derivatives, glycols, the various moistening, dispersing or emulsifying agents, and preservatives.

In the case of use of the compounds as an adjuvant treatment of antibiotic therapy or anti-viral therapy, the duration of treatment will for example be equal to or greater than that of the antibiotic therapy or of the anti-viral therapy. In other cases, the administration will be extended for a long time, for example 3 months to 2 years or more, and could be done in a discontinuous manner.

The compounds of formula I may be prepared by known methods such as described in U.S. Pat. No. 3,998,823.

In the following examples there are described several preferred embodiments to illustrate the invention. However, it should be understood that the invention is not intended to be limited to the specific embodiments.

EXAMPLE 1

Tablets were containing 200 mg of 8$\beta$-morpholinocarbonyl-4b$\alpha$, 8$\alpha$-dimethyl-12-isopropyl-(1$\beta$,2$\beta$,3$\beta$,4,4a$\beta$,4b$\alpha$,5,6,7,8,8a$\beta$, 9,10,10a-tetradecahydro-3,10a-ethenophenanthro-[1,2-c]-1'-(2-hydroxyethyl)-2',5'-pyrrolidinedione and sufficient excipient of lactose, starch, talc and magnesium stearate for a final tablet weight of 300 mg.

EXAMPLE 2

Tablets were prepared containing 200 mg of 8$\beta$-morpholinocarbonyl-4b$\alpha$,8$\alpha$-dimethyl-12-isopropyl-(1$\beta$,2$\beta$,3$\beta$,4,4a$\beta$,4b$\alpha$,5,6,7,8,8a$\beta$, 9,10,10a-tetradecahydro-3,10a-ethenophenanthro-[1,2-c]-2',5'-pyrrolidinedione (maleopimarimidyl) and sufficient excipient of lactose, starch talc and magnesium stearate for a final tablet weight of 300 mg.

EXAMPLE 3

An injectable solution was prepared containing 150 mg of 8$\beta$-morpholinocarbonyl-4b$\alpha$,8$\alpha$-dimethyl-12-isopropyl-1$\beta$,2$\beta$,3$\beta$,4, 4a$\beta$,4b$\alpha$,5,6, 7,8,8a$\beta$,9,10,10a-tetradecahydro-3,10a-ethenophenanthro-[1,2-c]-1'-(2-hydroxyethyl)-2',5'-pyrrolidinedione and sufficient aqueous solvent, q.s. for 2 ml.

EXAMPLE 4

An injectable solution was prepared containing 150 mg of 8$\beta$-morpholinocarbonyl-4b$\alpha$, 8$\alpha$-dimethyl-12-isopropyl-1$\beta$,2$\beta$,3$\beta$,4, 4a$\beta$, 4b$\alpha$,5,6,7,8,8a$\beta$, 9,10,10a-tetradecahydro-3,10a-ethenophenanthro-[1,2-c]-2',5'-pyrrolidinedione and sufficient aqueous solvent, q.s. for 2 ml.

EXAMPLE 5

Gelules were prepared containing 200 mg of 8$\beta$-morpholinocarbonyl-4b$\alpha$,8$\alpha$-dimethyl-12-isopropyl-1$\beta$, 2$\beta$,3$\beta$, 4,4a$\beta$,4b$\alpha$,5,6,7,8,8a$\beta$, 9,10,10a-tetradecahydro-3,10a-ethenophenanthro-[1,2-c]-1'-(2-hydroxyethyl)-2',5'-pyrrolidinedione and an excipient of mannite, citric acid, sodium chloride, thiurea, sodium diaminotetraacetate ethylene, lactose, methylcellulose and magnesium stearate, q.s. for one gelule.

EXAMPLE 6

An ointment was prepared containing 1.5 g of 8$\beta$-morpholinocarbonyl-4b$\alpha$, 8$\alpha$-dimethyl-12-isopropyl-1$\beta$, 2$\beta$, 3$\beta$, 4,4a$\beta$,4b$\alpha$, 5,6,7,8,8a$\beta$,9,10 10a-tetradecahydro-3,10a-ethenophenanthro-[1,2-c]-1'-(2-hydroxyethyl)-2',5'-pyrrolidinedione and excipients of cetyl alcohol, saturated vegetable triglycerides, esters of polyethylene glycol 2000 with fatty acids of 12 to 14 carbon atoms, Tween 80, paraoxybenzoates, sorbitol, carboxyvinyl polymer, sodium sulfite, triethanolamine, lecithin, purified water and lactic acid, q.s. for 100 g.

EXAMPLE 7

A cream was prepared containing 1.5 g of 8$\beta$-morpholinocarbonyl-4b$\alpha$,8$\alpha$, -dimethyl-12-isopropyl-1$\beta$, 2$\beta$,3$\beta$,4,4a$\beta$,4b$\alpha$,5,6,7,8,8a$\beta$, 9,10,10a-tetradecahydro-3,10a-ethenophenanthro-[1,2-c]-1'-(2-hydroxyethyl)-2',5'-pyrrolidinedione and sufficient excipients of 2-octyl-2-dodecanol alcohol, cetostearyl alcohol, sodium cetostearyl sulfate, methyl and propyl parahydroxybenzoates and purified water, q.s. for 100 g.

PHARMACOLOGICAL STUDY

The study was done with the following products:

PRODUCT A

8$\beta$-morpholinocarbonyl-4b$\alpha$,8$\alpha$-dimethyl-12-isopropyl-1$\beta$,2$\beta$,3$\beta$, 4,4a$\beta$,4b$\alpha$, 5,6,7,8,8a$\beta$-9,10,10a-tetradecahydro-3,10a-ethenophenanthro-[1,2-c]-1'(2-hydroxyethyl)-2',5'-pyrrolidinedione.

PRODUCT B

8$\beta$-morpholinocarbonyl-4b$\alpha$8$\alpha$-dimethyl-12-isopropyl-1$\beta$,2$\beta$,3$\beta$,4,4a$\beta$,4b$\alpha$, 5,6,7,8,8a$\beta$, 9,10,10a-tetradecahydro 3,10a-ethenophenanthro-[1,2-c]-2',5'-pyrrolidinedione.

1 Rosette test with red corpuscles of sheep

The administration to animals of a product revealed by an increase in their capacity to react to the injection of an immunizing product the ability to stimulate the activity of the immune systems. Male rats aged 3 months were sensitized intraperitoneally with sheep erythrocytes (day 0). 7 days later (day 7), their spleens were removed and the spleenocytes were put into contact with the erythrocytes of sheep. A count was then made of the percentage of leucocytes around which the erythrocytes had formed rosettes. The products under study were administered orally daily from day 1 to day 1. A dose of a product was considered to be immuno-stimulant if it multiplied by about 2 the percentage of rosettes observed in the control animals. The active doses for products A and B were 1 and 2 mg/kg, respectively, orally.

2 Test of antibody formation determination of the level of hemagglutinine in mice.

Mice received an intravenous administration of red corpuscles of sheep on the first day and the products were administered orally at a dose of 100 mg/kg from the 1st to the 3rd day. On the fourth day, the animals were killed and the levels of seral antibodies were determined by hemagglutination. With the product A, an increase of 23% of the level was observed as compared with the level of control animals.

3 Acute toxicity

The products tested were very well tolerated by rodents after acute oral administration. In fact, for product A, the LD 50 was 10 g/kg for the mouse and 6.3 g/kg for the rat, respectively.

Various modifications of the method of the invention may be made without departing from the spirit or scope thereof and it should be understood that the invention is intended to be limited only as defined in the appended claims.

What we claim is:

1. A method of inducing immunostimulating activity in warm-blooded animals in need of said activity comprising administering to warm-blooded animals in need of immunostimulating activity an effective immunostimulating amount of a maleo-pimaric acid compound of the formula

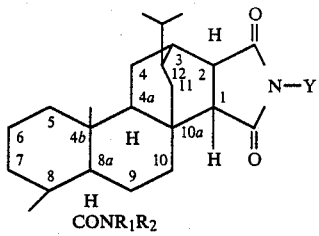

I

"wherein $R_1$ and $R_2$ together with the nitrogen atom form a group selected from the group consisting of morpholino, piperazin-1-yl, pyrrolididno, 4-alkylpiperazin-1-yl of 1 to 5 alkyl carbon atoms and 4-hydroxyalkyl-piperazin-1-yl of 1 to 5 alkyl carbon atoms and Y is selected from the group consisting of hydrogen, amino and B-hydroxythyl".

2. The method of claim 1 wherein $R_1$ and $R_2$ together with the nitrogen atom form morpholino.

3. The method of claim 1 wherein Y is hydrogen or β-hydroxyethyl.

4. The method of claim 1 wherein the compound is 8β-morpholinocarbonyl-4bα,8α-dimethyl-12-isopropl-1β,2β,3β,4,4aβ,4bα,5,6,7,8,8aβ,9,10,10a-tetradecahydro-3,10a-ethenophenanthro-[1,2-c]-1′-(2-hydroxyethyl)-2′, 5′-pyrrolidinedione.

5. The method of claim 1 wherein the compound is 8β-morpholinocarbonyl-4bα,8α-dimethyl-12-isopropyl-1β,2β,3β,4,4aβ,4bα,5,6,7,8,8aβ9, 10,10a-tetradecahydro-3,10a-ethenophenophenanthro-[1,2-c]-2′,5′-pyrrolidinedione.

* * * * *

UNITED STATES PATENT AND TRADEMARK OFFICE
CERTIFICATE OF CORRECTION

PATENT NO. : 4,880,803
DATED : Nov. 14, 1989
INVENTOR(S) : FRANCOIS DELEVALLEE, ROGER DERAEDT and JOSETTE BENZONI It is certified that error appears in the above-identified patent and that said Letters Patent is hereby corrected as shown below:

Col.   Line    Abstract
[57]

" 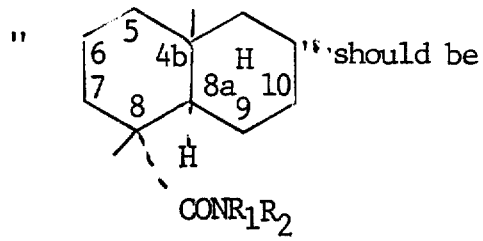 " should be

-- 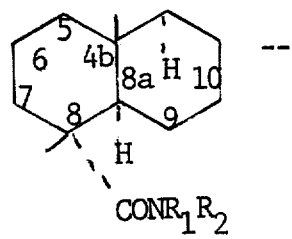 --

1      Formula I    " 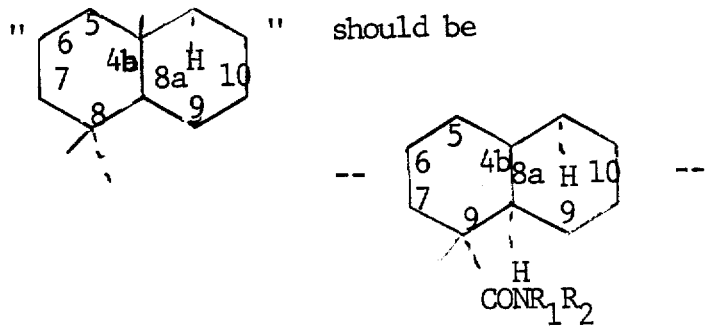 should be --

UNITED STATES PATENT AND TRADEMARK OFFICE
CERTIFICATE OF CORRECTION

PATENT NO. : 4,880,803

DATED : Nov. 14, 1989

INVENTOR(S) : FRANCOIS DELEVALLE, ROGER DERAEDT and JOSETTE BENZONI

It is certified that error appears in the above-identified patent and that said Letters Patent is hereby corrected as shown below:

| Col. | Line | |
|---|---|---|
| 2 | 28 | "β" should be -- α -- |
| 2 | 32 | Left out "4b α" after 4,4a β |
| 2 | 48 | See Amendment dated March 2, 1989 Cancel "," and insert --and-- |
| 5 | Claim 1 | |

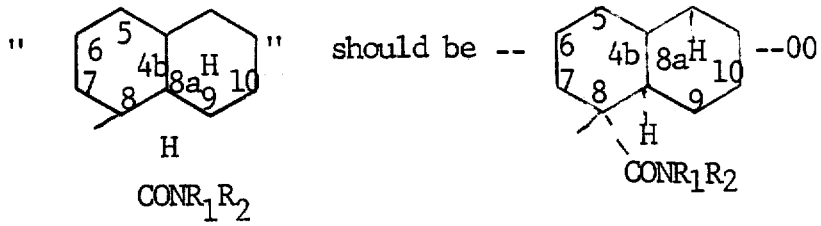

Signed and Sealed this

Twelfth Day of February, 1991

Attest:

HARRY F. MANBECK, JR.

*Attesting Officer*    *Commissioner of Patents and Trademarks*